United States Patent
Cano et al.

(10) Patent No.: US 12,420,322 B2
(45) Date of Patent: Sep. 23, 2025

(54) COMPOSITIONS AND METHODS FOR BIOREMEDIATION OF GLYPHOSATE CONTAINING SUBSTRATES

(71) Applicant: ANCIENT ORGANICS BIOSCIENCE, INC., San Luis Obispo, CA (US)

(72) Inventors: Raul De Jesus Cano, San Luis Obispo, CA (US); Don Morgan Huber, Melba, ID (US); Martha R. Carlin, Lonetree, CO (US)

(73) Assignee: Ancient Organics Bioscience, Inc., San Luis Obispo, CA (US)

( * ) Notice: Subject to any disclaimer, the term of this patent is extended or adjusted under 35 U.S.C. 154(b) by 702 days.

(21) Appl. No.: 17/780,789

(22) PCT Filed: Nov. 25, 2020

(86) PCT No.: PCT/US2020/062248
§ 371 (c)(1),
(2) Date: May 27, 2022

(87) PCT Pub. No.: WO2021/108566
PCT Pub. Date: Jun. 3, 2021

(65) Prior Publication Data
US 2022/0410233 A1 Dec. 29, 2022

Related U.S. Application Data

(60) Provisional application No. 62/941,084, filed on Nov. 27, 2019.

(51) Int. Cl.
*B09C 1/10* (2006.01)
*C12N 1/20* (2006.01)

(52) U.S. Cl.
CPC ............ *B09C 1/10* (2013.01); *C12N 1/205* (2021.05); *B09C 2101/00* (2013.01)

(58) Field of Classification Search
CPC .................................................. B09C 2101/00
See application file for complete search history.

(56) References Cited

U.S. PATENT DOCUMENTS

| | | |
|---|---|---|
| 2010/0199363 A1 | 8/2010 | Hartley et al. |
| 2012/0329650 A1 | 12/2012 | Lopez-Cervantes |
| 2015/0191756 A1 | 7/2015 | Sato et al. |
| 2017/0008814 A1 | 1/2017 | Bortoli |
| 2019/0183131 A1 | 6/2019 | Kendirgi et al. |

OTHER PUBLICATIONS

Mousa, N. et al. "Bacillus Megaterium biodegradation glyphoate", Iraqi J Agric Sci, 2019:50(6):1674-1680. (Year: 2019).*
Moneke, A. et al., "Biodegradation of glyphosate herbicide in vitro using bacterial isolates from four rice fields", African J Biotech vol. 9 (26), pp. 4067-4074, Jun. 28, 2010. (Year: 2010).*
Quinn, J. et al. "Carbon-phosphorus bond cleavage by Gram-positive and Gram-negative soil bacteria", Appl Microbiol Biotechnol (1989) 31:283-287. (Year: 1989).*

* cited by examiner

*Primary Examiner* — Gina C Justice

(57) ABSTRACT

Disclosed are novel bioremediation formulations and inocula for formulation of bioremediation formulations. The formulations of the present disclosure comprise viable microorganisms of the species *Paenibacillus xylanexedens, Pseudomonas fluorescens, Bacillus safensis, Streptomyces griseus, Micrococcus luteus,* and *Bacillus megaterium* and can be used to degrade glyphosate residue associated with a substrate contaminated with glyphosate, and thereby remedially treat the substrate. Related methods are also disclosed.

20 Claims, 8 Drawing Sheets glyphosate

FIG. 1A glyoxylate

FIG. 1B

AMPA

FIG. 1C phosphono-
formaldehyde

FIG. 1D sarcosine

FIG. 1E glycine

FIG. 1F

α-D-ribose-1-[N-(phosphonomethyl)glycine] 5-triphosphate

FIG. 2A

α-D-ribose-1-[N-(phosphonomethyl)glycine] 5-monophosphate

FIG. 2B

5-phospho-α-D-ribose 1,2-cyclic phosphate

FIG. 2C

α-D-ribose 1,5-bisphosphate

FIG. 2D

5-phospho-α-D-ribose 1-diphosphate

COMPOSITIONS AND METHODS FOR BIOREMEDIATION OF GLYPHOSATE CONTAINING SUBSTRATES

RELATED APPLICATION

This application claims the benefit of U.S. Provisional Patent Application No. 62/941,084 filed Nov. 27, 2019; the entire contents of Patent Application 62/941,084 is hereby incorporated by reference.

FIELD OF THE DISCLOSURE

The present disclosure relates to bioremediation. The present disclosure further relates to compositions and methods for bioremediation of substrates containing glyphosate.

BACKGROUND OF THE DISCLOSURE

The following paragraphs are provided by way of background to the present disclosure. They are not, however, an admission that anything discussed therein is prior art or part of the knowledge of persons skilled in the art.

The growth of weed plants can reduce the amount of resources available to cultivated plants and can, therefore, have a negative effect on the cultivated plants' quality or yield. As a result, a multiplicity of chemical herbicides has evolved to control the growth of undesirable plants. One well known and widely applied chemical herbicide is the organophosphate N-(phosphonomethyl)glycine, also commonly known as glyphosate and marketed in various commercial formulations, including under the trade name Roundup®. Glyphosate containing herbicidal formulations can be classified as broad spectrum, systemic, herbicidal formulations that are known to exhibit a herbicidal effect against a wide variety of weed plant species, including, for example, annual broadleaf weeds and perennial grasses competing with the growth of crop plants.

In physiological terms, glyphosate formulations act by initially being absorbed by the growing plant's aboveground tissue, i.e. the stems and leaves or other photosynthesizing tissues, when applied thereto, for example, in the form of a sprayable herbicidal formulation. After absorption by the plant's tissues, the active glyphosate compound is systemically dispersed throughout the plant and interferes with a vital aspect of the plant's cellular metabolism. In particular, in glyphosate treated plants aromatic amino acid biosynthesis in a metabolic pathway, present in almost all plants and known as the shikimate pathway, becomes substantially compromised so that plants treated with glyphosate generally exhibit visually apparent phytotoxic effects or burndown symptoms such as yellowing or browning. When exposed to lethal quantities of glyphosate, plants will wilt and die, generally over a period of days or weeks following application of the herbicide.

The effectiveness of glyphosate as a herbicide has resulted in a significant agricultural and horticultural use of glyphosate based herbicidal products in the U.S. and elsewhere. Following the first registration of glyphosate for herbicidal use in 1974, sales and use of glyphosate based herbicides have steadily increased. Thus, it has been estimated that farm sector glyphosate use in the United States rose from between 6 and 8 million pounds in 1987 to 180 to 185 million pounds in 2007, and to a further 240 million pounds in 2014. In addition, glyphosate based herbicides account for the majority (53.5%) of total farm based herbicide use (Myers et al., 2016, Environmental Health 15:19).

However, the large scale use of glyphosate based herbicides has resulted in significant concerns regarding the environmental impact and toxicological effects on non-target species. Thus, for example, the cancer agency International Agency for Research on Cancer (IARC) of the World Health Organization (WHO, Geneva, Switzerland) in 2015 classified glyphosate as "probably carcinogenic to humans" (IARC Monograph V. 112, 2015). Furthermore, acting on the reporting of the IARC, several countries recently have taken steps to restrict or ban the use of glyphosate herbicides over human health concerns (see: e.g. Avramova, N.: Austrian Lawmakers Vote to Ban Weed Killer Glyphosate. CNN. 3 Jul. 2019. https://www.cnn.com/2019/07/03/health/austria-glyphosate-ban-weed-killer-bayer-intl/index.html (accessed, Oct. 9, 2019)).

In light of the adverse health and environmental effects attributable to glyphosate exposure, a need has emerged for techniques to detoxify glyphosate, including, for example, techniques for the remedial treatment of glyphosate contaminated samples and environmental sites, such as soil, ground water and surface water sites. Remedial treatment techniques are particularly needed since glyphosate is not readily biodegradable, with glyphosate half-lives ($DT_{50}$) in water and soil field studies ranging from a few days to several months, a year, or even much longer, depending on soil composition (Torretta, V. et al., Sustainability, 2018, 10, 950; Székács A. et al., 2012, http://www.intechopen.com/books/herbicides-properties-synthesis-and-control-of-weeds/forty-years-with-glyphosate (accessed, Oct. 9, 2019); Huber, 2010, Fluid J. 18 (3) #69); Eberbach, P., 1998. Pesticide Science 52, 229-240; Kools, S. A. E. et al., 2005, Soil Biology & Biochemistry 37, 2005, 1303-1307; Valle, A. L. et al., Environmental Chemistry Letters, 2019, 17(1) 291-317). High environmental glyphosate concentrations can therefore persist for longer periods of time at contaminated sites than was initially proposed, and for longer periods of time than is deemed desirable.

There is, therefore, a need in the art for compositions and processes imparting the degradation of herbicidal compounds, and, in particular, there is a need for compositions and processes for the biodegradation of glyphosate.

SUMMARY OF THE DISCLOSURE

The following paragraphs are intended to introduce the reader to the more detailed description that follows and not to define or limit the claimed subject matter of the present disclosure.

In one broad aspect, the present disclosure relates to compositions for the bioremediation of substrates containing glyphosate. Accordingly, in one aspect, the present disclosure provides, in accordance with the teachings herein, in at least one embodiment, a microbial inoculum comprising cultured viable microorganisms of the species *Paenibacillus xylanexedens, Pseudomonas fluorescens, Bacillus safensis, Streptomyces griseus, Micrococcus luteus*, and *Bacillus megaterium*.

In at least one embodiment, the microbial inoculum can further comprise one or more cultured viable microorganisms selected from the species *Rhanella aquatilis* and *Bacillus marisflavus*.

In at least one embodiment, the microbial inoculum can further comprise cultured viable microorganisms of each of the species *Rhanella aquatilis* and *Bacillus marisflavus*.

In at least one embodiment, the microbial inoculum can further comprise cultured viable microorganisms of each of the species *Rhanella aquatilis* and *Bacillus marisflavus*.

In at least one embodiment, the microbial inoculum can further comprise cultured viable microorganisms of at least one of the species *Acetobacter* spp., *Bacillus cereus*, *Bacillus oceanisediminis*, *Bacillus thuringiensis*, *Bacillus wiedmannii*, *Clostridium innoccuum*, *Kribella flavida*, *Lactobacillus plantarum*, *Obesumbacterium proteus*, and *Serratia liquefaciens*.

In at least one embodiment, the microbial inoculum can comprise from about 1×10^2 CFU per ml or per gram to about 1×10^8 CFU per ml or per gram of each of the microorganisms.

In at least one embodiment, the microbial inoculum can further comprise a diluent.

In at least one embodiment, the diluent can be a saline solution.

In at least one embodiment, the microbial inoculum can further comprise a cryoprotectant.

In at least one embodiment, the cryoprotectant can be glycerol in an amount of from about 10% (v/v) to about 35% (v/v).

In at least one embodiment, the microbial inoculum of cultured viable microorganisms can be dehydrated.

In accordance with another aspect, the presents disclosure provides bioremediation formulations. Accordingly, in one aspect, the present disclosure provides, in at least one embodiment, a bioremediation formulation for application to a residual glyphosate containing substrate, the bioremediation formulation comprising a microbial inoculum comprising cultured viable microorganisms of the species *Paenibacillus xylanexedens, Pseudomonas fluorescens, Bacillus safensis, Streptomyces griseus, Micrococcus luteus,* and *Bacillus megaterium*, together with a carrier.

In at least one embodiment, the carrier can be a mineral earth; a polysaccharide; a plant seed, wood or nutshell meal; a grain flour; peat or a peat derived product; or compost.

In at least one embodiment, the carrier can be diatomaceous earth, gypsum, vermiculite, attapulgite, cellulose, hydroxyethyl cellulose, carboxymethyl cellulose, alginate, or lignite powder.

In at least one embodiment, the microbial inoculum together with an optional diluent and the carrier can constitute at least about 95% (w/w) of the bioremediation formulation.

In at least one embodiment, the bioremediation formulation, following application to the glyphosate containing substrate, can biodegrade glyphosate to generate one or more breakdown products selected from aminomethyl phosphonic acid (AMPA), sarcosine, glyoxal, glycine, N-acetylglycine, formaldehyde, and phosphonoformaldehyde.

In at least one embodiment, the bioremediation formulation, following application to the glyphosate containing substrate, can biodegrade glyphosate to generate one or more breakdown products selected from α-D-ribose-1-[N-(phosphonomethyl)glycine] 5-triphosphate, α-D-ribose-1-[N-(phosphonomethyl)glycine] 5-monophosphate, 5-phospho-α-D-ribose 1,2 cyclic phosphate, α-D-ribose 1,5 biphosphate, and 5-phospho-α-D-ribose 1-diphosphate.

In at least one embodiment, the microorganisms in the microbial inoculum can include a microbial amino acid metabolism which is not inhibited by glyphosate.

In at least one embodiment, the microbial inoculum can further comprise cultured viable microorganisms of at least one of the species *Acetobacter* spp., *Bacillus cereus*, *Bacillus oceanisediminis*, *Bacillus thuringiensis*, *Bacillus wiedmannii*, *Clostridium innoccuum*, *Kribella flavida*, *Lactobacillus plantarum*, *Obesumbacterium proteus*, and *Serratia liquefaciens*.

In at least one embodiment, the substrate can be a solid substrate.

In at least one embodiment, the substrate can be a liquid substrate.

In at least one embodiment, the solid substrate can be soil.

In at least one embodiment, the liquid substrate can be water, and the microbial inoculum can further comprise cultured viable microorganisms of each of the species *Rhanella aquatilis* and *Bacillus marisflavis*.

In at least one embodiment, the liquid substrate can be surface water or ground water.

In accordance with another aspect, the present disclosure provides methods for bioremediation. Accordingly, in one aspect, the present disclosure provides, in at least one embodiment, a method for bioremediation of a residual glyphosate containing substrate, the method comprising:

(a) contacting a residual glyphosate containing substrate with a bioremediation formulation comprising a microbial inoculum comprising cultured viable microorganisms of the species *Paenibacillus xylanexedens, Pseudomonas fluorescens, Bacillus safensis, Streptomyces griseus, Micrococcus luteus,* and *Bacillus megaterium*, the microorganisms remaining viable when the microbial inoculum is contacted with the glyphosate containing substrate; and (b) maintaining contact between the residual glyphosate containing substrate and the bioremediation formulation for a sufficient period of time for the microorganisms to microbially biodegrade the residual glyphosate.

In at least one embodiment, the bioremediation formulation can comprise a bioremedially effective amount of the microbial inoculum.

In at least one embodiment, the bioremediation formulation following application to the glyphosate containing substrate, can biodegrades glyphosate to generate one or more breakdown products selected from aminomethyl phosphonic acid (AMPA), sarcosine, glyoxal, glycine, N-acetylglycine, formaldehyde and phosphonoformaldehyde.

In at least one embodiment, the bioremediation formulation, following application to the glyphosate containing substrate, can biodegrade glyphosate to generate one or more breakdown products selected from α-D-ribose-1-[N-(phosphonomethyl)glycine] 5-triphosphate, α-D-ribose-1-[N-(phosphonomethyl)glycine] 5-monophosphate, 5-phospho-α-D-ribose 1,2 cyclic phosphate, α-D-ribose 1,5 biphosphate, and 5-phospho-α-D-ribose 1-diphosphate.

In at least one embodiment, the microorganisms in the microbial inoculum can include a microbial amino acid metabolism which is not inhibited by glyphosate.

In at least one embodiment, the substrate can be a solid substrate.

In at least one embodiment, the substrate can be a liquid substrate.

In at least one embodiment, the solid substrate can be soil.

In at least one embodiment, the liquid substrate can surface water or ground water.

In accordance with another aspect, the presents disclosure provides methods for forming a bioremediation formulation. Accordingly, in one aspect, the present disclosure provides, in at least one embodiment, a method of forming a bioremediation formulation comprising contacting a microbial inoculum comprising cultured viable microorganisms of the species *Paenibacillus xylanexedens, Pseudomonas fluore-* scens, *Bacillus safensis, Streptomyces griseus, Micrococcus luteus*, and *Bacillus megaterium* with a carrier to thereby form a bioremediation formulation.

In at least one embodiment, the carrier can be a mineral earth; a polysaccharide; a plant seed, wood or nutshell meal; a grain flour; peat or a peat derived product; or compost.

In at least one embodiment, the carrier can be cellulose, hydroxyethyl cellulose, carboxymethyl cellulose, gypsum, vermiculite, attapulgite, diatomaceous earth, lignite powder, peat, or alginate.

In accordance with another aspect, the presents disclosure provides a bioremediation kit. Accordingly, in one aspect, the present disclosure provides, in at least one embodiment, a kit comprising a microbial inoculum comprising cultured viable microorganisms of the species *Paenibacillus xylanexedens, Pseudomonas fluorescens, Bacillus safensis, Streptomyces griseus, Micrococcus luteus*, and *Bacillus megaterium*, together with instructions for use of the kit for application to a residual glyphosate containing substrate.

In at least one embodiment, the kit can comprise a concentrated microbial inoculum and a diluent, to prepare a diluted microbial inoculum.

In at least one embodiment, the kit can comprise a carrier to formulate a bioremediation formulation comprising a bioremedially effective amount of the microbial inoculum.

In at least one embodiment, the kit can comprise a concentrated bioremediation formulation and a diluent, to prepare a bioremedially effective bioremediation formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

The figures together with the following detailed description make apparent to those skilled in the art how the disclosure may be implemented in practice.

DETAILED DESCRIPTION OF THE DISCLOSURE

Various compositions, methods or processes will be described below to provide an example of an embodiment of each claimed subject matter. No embodiment described below limits any claimed subject matter and any claimed subject matter may cover processes, compositions or methods that differ from those described below. The claimed subject matter is not limited to compositions, processes or methods having all of the features of any one composition, system or process described below or to features common to multiple or all of the compositions, systems or methods described below. It is possible that a composition, method or process described below is not an embodiment of any claimed subject matter. Any subject matter disclosed in a composition, method or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such as "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either". The term "and/or" is intended to represent an inclusive or. That is "X and/or Y"

is intended to mean X or Y or both, for example. As a further example, X, Y, and/or Z is intended to mean X or Y or Z or any combination thereof.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore, any range of values described herein is intended to specifically include the limiting values of the range, and any intermediate value or sub-range within the given range, and all such intermediate values and sub-ranges are individually and specifically disclosed (e.g. a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent or patent application was specifically and individually indicated to be incorporated by reference in its entirety.

Terms and Definitions

Figure 1A:
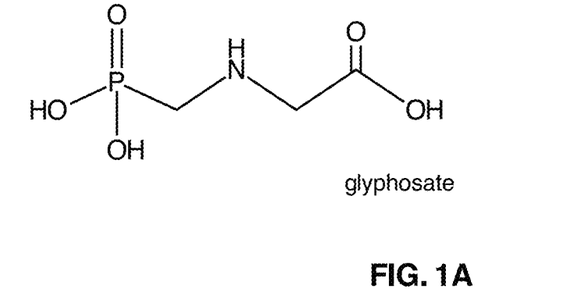
FIGS. 1A-1F depict the chemical structures of certain chemical compounds as follows: glyphosate (FIG. 1A); glyoxylate (FIG. 1B); aminomethyl phosphonic acid (AMPA) (FIG. 1C); phosphonoformaldehyde (FIG. 1D); sarcosine (FIG. 1E); and glycine (FIG. 1E).

The terms "glyphosate" and "N-(phosphonomethyl)glycine", as may be used interchangeably herein, mean the chemical compound shown in FIG. 1A, and includes further its anionic or zwitterionic forms which in an aqueous solutions may be provided along with a suitable cation, and salts thereof, such as ammonium salt e.g. diammonium salt, amine salts, e.g. isopropyl amine salt, potassium salt, sodium salt, or sulfonium salt, e.g. trimethyl sulfonium salt, or combinations thereof. It is further noted that the term "residual" may be used herein in combination with glyphosate. The term residual is intended to refer to quantities of glyphosate which have not acted as an herbicide and have accumulated to non-natural concentrations in or on a substrate.

Figure 1B:
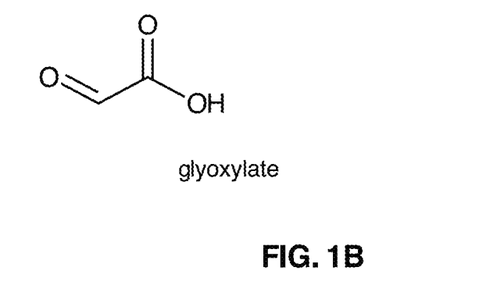

The term "glyoxylate", as used herein, means the compound shown in FIG. 1B and includes its ionic forms and salts thereof.

Figure 1C:
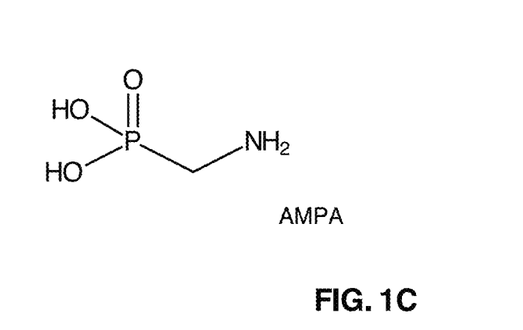

The terms and "aminomethyl phosphonic acid" and "AMPA", as may be used interchangeably herein, means the compound shown in FIG. 1C and includes its ionic forms and salts thereof.

Figure 1D:
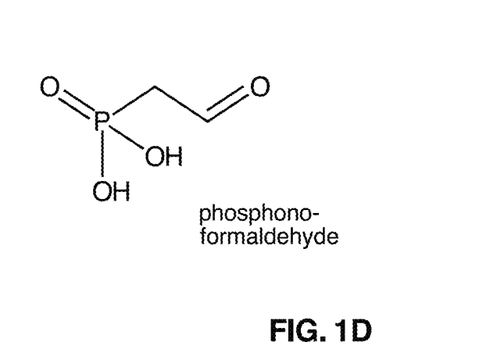

The term "phosphonoformaldehyde", as used herein, means the compound shown in FIG. 1D and includes its ionic forms and salts thereof.

Figure 1E:
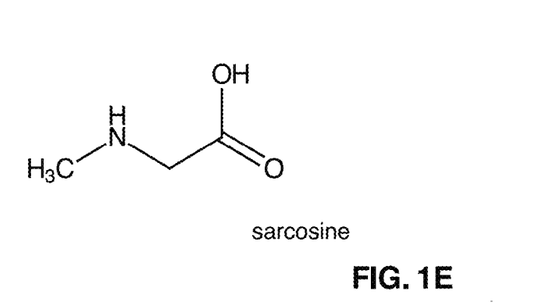

The term "sarcosine", as used herein, means the compound shown in FIG. 1E and includes its ionic forms and salts thereof.

Figure 1F:
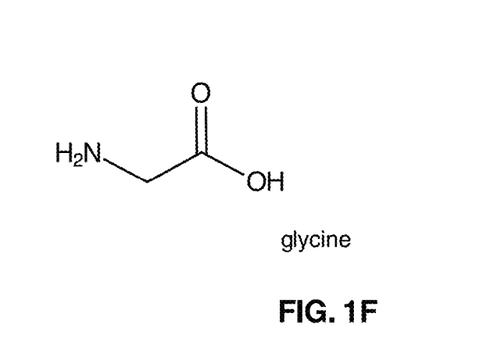

The term "glycine", as used herein, means the compound shown in FIG. 1F and includes its ionic forms and salts thereof.

Figure 2A:
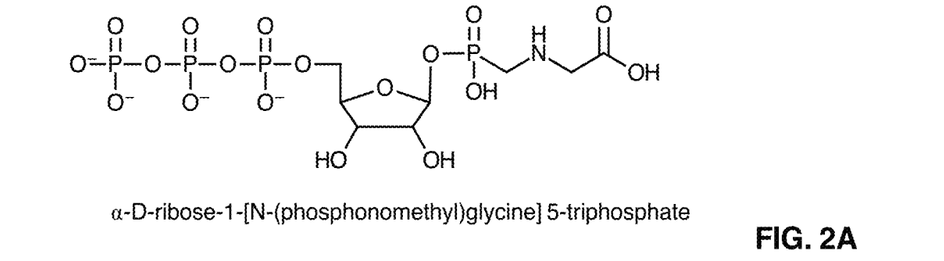
FIGS. 2A-2E depict the chemical structures of certain chemical compounds as follows: α-D-ribose-1-[N-(phosphonomethyl)glycine] 5-triphosphate (FIG. 2A); α-D-ribose-1-[N-(phosphonomethyl)glycine] 5-monophosphate (FIG. 2B); 5-phospho-α-D-ribose 1,2 cyclic phosphate (FIG. 2C); α-D-ribose 1,5 biphosphate (FIG. 2D); and 5-phospho-α-D-ribose 1-diphosphate (FIG. 2E).

The term "α-D-ribose-1-[N-(phosphonomethyl)glycine] 5-triphosphate", as used herein, means the compound shown in FIG. 2A and includes its ionic forms and salts thereof.

Figure 2B:
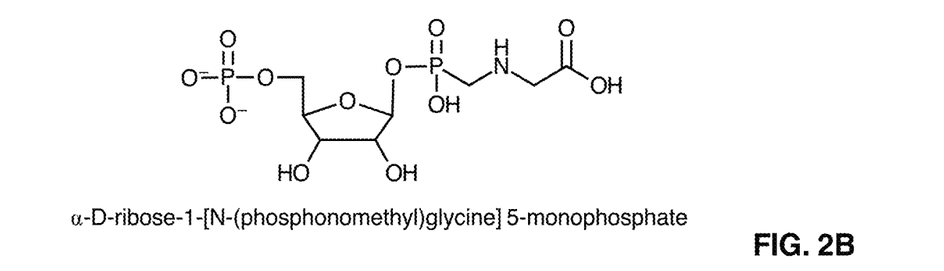

The term "α-D-ribose-1-[N-(phosphonomethyl)glycine] 5-monophosphate", as used herein, means the compound shown in FIG. 2B and includes its ionic forms and salts thereof.

Figure 2C:
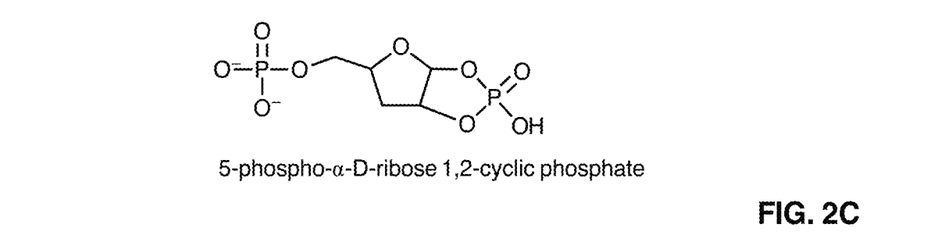

The terms and "5-phospho-α-D-ribose 1,2 cyclic phosphate", as may be used interchangeably herein, means the compound shown in FIG. 2C and includes its ionic forms and salts thereof.

Figure 2D:
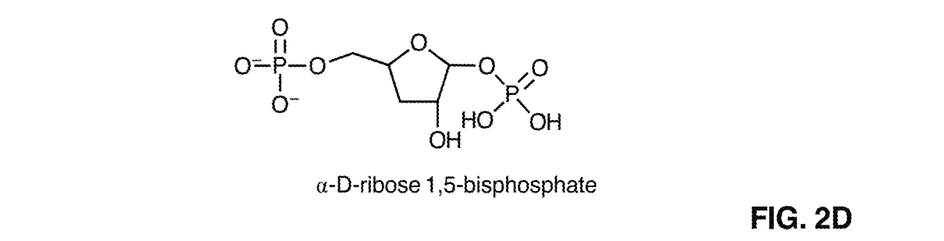

The term "α-D-ribose 1,5 biphosphate", as used herein, means the compound shown in FIG. 2D and includes its ionic forms and salts thereof.

Figure 2E:
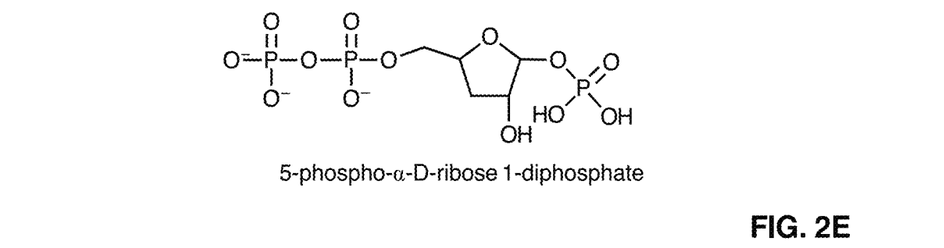

The term "5-phospho-α-D-ribose 1-diphosphate", as used herein, means the compound shown in FIG. 2E and includes its ionic forms and salts thereof.

The term "cultured", as used herein, refers to one or more microorganisms isolated from a natural environment in which the microorganism(s) occur, and held under conditions suitable to propagate the microorganisms outside the natural environment, for example, in a laboratory.

The terms "inoculum" or "microbial inoculum", as used herein, refer to a pure or mixed culture microorganism-based product capable of microbial propagation, and that can be used, for example, as a seed culture, to inoculate a medium or substrate.

The term "bioremedially effective amount", as used herein, refers to an amount of a formulation sufficient to remedially treat a substrate contaminated with an undesirable chemical compound, for example, a toxic compound, to cause natural agents, microorganisms, for example, included in the formulation to facilitate the breakdown of the undesirable compound into other chemical compounds, to thereby reduce the quantities of the undesirable chemical compound associated with the substrate, and can fall in relatively wide range that can be determined by routine trials.

Microorganisms are referred to herein by Latin names in accordance with the Linnaean taxonomic biological classification system. Accordingly, reference is made to microorganisms which can be identified with reference to certain genus, species, subspecies and strain names. In each instance, non-genetically modified and genetically modified microorganisms are intended to be included.

General Implementation

As hereinbefore mentioned, the present disclosure relates to compositions and methods for the bioremedial treatment of substrates containing glyphosate. The compositions and methods of the present disclosure permit the breakdown of glyphosate in breakdown products which are less hazardous than glyphosate, and thus treatment of the substrate with the compositions of the present disclosure can result in the decontamination of the substrate. Formulations of the present disclosure when applied to a glyphosate containing substrate substantially increase the degradation rate of glyphosate when compared to untreated substrates, thereby limiting the environmental or human exposure risks. One further attractive feature of the present disclosure, is that the compositions of the present disclosure can be formulated using naturally occurring microorganisms.

In what follows specific example embodiments are described.

In accordance herewith, in one aspect, the present disclosure provides, in at least one embodiment, a microbial inoculum comprising cultured viable microorganisms of the species *Paenibacillus xylanexedens, Pseudomonas fluorescens, Bacillus safensis, Streptomyces griseus, Micrococcus luteus,* and *Bacillus megaterium.*

In another aspect, the present disclosure provides a bioremedial formulation comprising a microbial inoculum comprising cultured viable microorganisms of the species *Paenibacillus xylanexedens, Pseudomonas fluorescens, Bacillus safensis, Streptomyces griseus, Micrococcus luteus,* and *Bacillus megaterium,* together with a carrier.

The microbial inoculum can additionally include further microorganisms. Thus, for example, in one embodiment, the microbial inoculum can additionally comprise one or more cultured viable microorganisms selected from the species *Rhanella aquatilis* and *Bacillus marisflavus.*

In another embodiment, the microbial inoculum can additionally comprise cultured viable microorganisms of each of the species *Rhanella aquatilis* and *Bacillus marisflavus.*

In another embodiment, the microbial inoculum can additionally comprise cultured viable microorganisms of one or more of the species *Acetobacter* spp., *Bacillus cereus, Bacillus oceanisediminis, Bacillus thuringiensis, Bacillus wiedmannii, Clostridium innoccuum, Kribella flavida, Lactobacillus plantarum, Obesumbacterium proteus,* and *Serratia liquefaciens.*

It is noted that the microbial metabolism of the microorganisms included in the microbial inoculum is not lethally inhibited by glyphosate. In this respect, it is noted that glyphosate is known to inhibit certain types of naturally occurring amino acid metabolism pathways, including, notably, aromatic amino acid metabolism pathways occurring in plants, and including aromatic amino acid metabolism pathways including an enzyme known as enolpyruvylshikimate-3-phosphate synthase (EPSPS), encoded by a gene known as AroA. The microorganisms in the microbial inoculum of the present disclosure may lack AroA genes and therefore EPSPS, or if they do include AroA genes encoding EPSPS, the specific EPSPS present in the microorganism may be a variant which is insensitive to inhibition by glyphosate.

Initially, in an aspect hereof, in order to prepare the formulations of the present disclosure, a microbial inoculum comprising certain microorganisms, notably, at least, the microbial species *Paenibacillus xylanexedens, Pseudomonas fluorescens, Bacillus safensis, Streptomyces griseus, Micrococcus luteus,* and *Bacillus megaterium,* is prepared. In an aspect hereof, a substantially pure aliquot of each of the microorganisms of the present disclosure can be obtained from a microorganism culture collection, for example, from the American Type Culture Collection (ATCC), the Agricultural Research Service (ARS) Culture Collection (NRRL), or a similar collection, or from private companies such as BioSource Flavors Inc., The BioCollective, LLC, Pure Cultures Inc., Nutraceutix Inc, or PaleoBiotica, Inc., for example. ATCC or NRRL culture catalogue numbers are as follows: *Paenibacillus xylanexedens* (NRRL: B-51090), *Pseudomonas fluorescens* (ATCC: 13525), *Bacillus safensis* (ATCC: BAA1128), *Streptomyces griseus* (ATCC: 10137; 13273; 13968; 21483; 27419; 39208), *Micrococcus luteus* (ATCC: 4698; 10240; 15220), and *Bacillus megaterium* (ATCC: 9885; 12872; 14581; 19213). The aliquot can be provided in various forms, for example, as a dry powder, or freeze dried viable cells, a glycerol stock of viable cells, a liquid culture of viable cells, a dried liquid culture, or a stab culture. Upon obtaining an aliquot of a microorganism a quantity thereof can be used to inoculate a suitable growth medium and the microorganisms can be grown in quantities, as desired, and cultured under appropriate conditions, for example in a liquid growth medium comprising appropriate microbial nutrients under growth promoting conditions. Thereafter the microorganisms can be harvested under conditions ensuring that viable microorganisms are retained from the medium, and the harvested microorganisms can be used to prepare the bioremediation formulations of the present disclosure.

In some embodiments, the species included in the formulation can be co-cultured, or alternatively, the species can initially be separately grown and mixed upon harvesting. General growing conditions for cultivating and growing the microbial species of the present disclosure include growth on agar based media, such as MRS agar or MRS liquid media, as described in de Man, J. D.; Rogosa, M.; Sharpe, M. E. (1960): "A Medium for the Cultivation of Lactobacilli", J. Appl Bact. 23 (130-135). *Paenibacillus xylanexedens, Pseudomonas fluorescens, Bacillus safensis, Bacillus megaterium, Streptomyces griseus, Micrococcus luteus, Rhanella aquatilis,* and *Bacillus marisflavis* may all be grown using sterile MRS growth media, or modifications thereof. Further growth media that may be used include Trypticase Soy Broth (TSB), Nutrient Broth, Luria-Bertine broth (LB-broth), and ISP medium #1, or modifications thereof.

MRS growth medium can contain, for example:
1.0% peptone
1.0% beef extract
0.4% yeast extract
2.0% glucose
0.5% sodium acetate trihydrate
0.1% polysorbate 80 (also known as Tween 80)
0.2% dipotassium hydrogen phosphate
0.2% triammonium citrate
0.02% magnesium sulfate heptahydrate
0.005% manganese sulfate tetrahydrate
1.0% agar
pH adjusted to 6.2 at 25° C.
TSB growth medium can contain, for example:
Tryptone (Pancreatic Digest of Casein) 17.0 g/L water
Soytone (Peptic Digest of Soybean) 3.0 g/L water
Glucose (=Dextrose) 2.5 g/L water
Sodium Chloride 5.0 g/L water
Dipotassium phosphate 2.5 g/L water
pH 7.3±0.2
Nutrient Broth can contain, for example:
Beef extract 3 g/L water
Peptone 5 g/L water
LB broth can contain, for example:
Peptone 140 10 g/L water;
Yeast extract 5 g/L water,
NaCl 5 g/L water
ISP medium #1 can contain, for example:
ISP #1: Tryptone (BD 211705) 5.0 g/L water
Yeast extract 3.0 g/L water
Agar (optional) 15.0 g/L water.
Growth conditions may vary but can include, for example, growth in a flask or other suitable growth vessel containing liquid MRS or MRS agar inoculated with an inoculating quantity of a microorganism, between 20° C. and 37° C., for a period of 12-36 hrs under agitation, such as, for example, imparted by a temperature controlled standard incubator-shaker for the cultivation of microorganisms, as will be known to those of skill in the art. If desired, larger quantities of the microorganisms may be obtained by scaling up growth and recovery equipment and increasing the quantities of growth media, for example, by using fermentation equipment, such as bioreactors and fermenters. Further guidance regarding growth of microorganisms in bioreactors may be found in for example: H. P. Meyer et al. in: Industrial Biotechnology: Products and Processes, 2017, First Edition, Whittmann and Liao, Wiley-VCH Verlag GmbH.

In order to prepare the microbial inoculum of the present disclosure, a quantity of each *Paenibacillus xylanexedens, Pseudomonas fluorescens, Bacillus safensis, Streptomyces griseus, Micrococcus luteus*, and *Bacillus megaterium* is obtained and mixed to obtain a microbial inoculum including each of the microbial species *Paenibacillus xylanexedens, Pseudomonas fluorescens, Bacillus safensis, Streptomyces griseus, Micrococcus luteus*, and *Bacillus megaterium*. In one embodiment, a microbial inoculum of each *Paenibacillus xylanexedens, Pseudomonas fluorescens, Bacillus safensis, Streptomyces griseus, Micrococcus luteus*, and *Bacillus megaterium* is obtained in a concentration sufficient to prepare a microbial inoculum comprising a bioremedially effective amount of the microorganisms, for example, a microbial inoculum that allows a finished bioremediation formulation to comprise from about $1\times10^2$ Colony Forming Units (CFU) to about $1\times10^8$ CFU per ml or per gram of each species, including, for example, $1\times10^3$ CFU, $1\times10^4$ CFU, $1\times10^5$ CFU, $1\times10^6$ CFU, or $1\times10^7$ CFU per ml or per gram. CFU quantification may be performed using suitable assays known to the art, see e.g. Goldman E., Green, L. Practical Handbook of Microbiol., $2^{nd}$ Ed. USA: CRC Press, Taylor and Francis Group; Siewerts et al., 2008, Letters in App. Microbiol. 47, 275-278. As will be understood by those of skill in the art, this may involve the use of a suitable diluent such as, for example, a sterile saline (0.9% NaCl) solution, water, or growth medium, for example. In this manner, a microbial inoculum comprising each of *Paenibacillus xylanexedens, Pseudomonas fluorescens, Bacillus safensis, Streptomyces griseus, Micrococcus luteus*, and *Bacillus megaterium* can be obtained.

Optional additional microbial organisms that may be included in the microbial inoculum include *Rhanella aquatilis* and *Bacillus marisflavus*.

Optional further additional microbial organisms that may be included in the microbial inoculum include *Acetobacter* spp., *Bacillus cereus, Bacillus oceanisediminis, Bacillus thuringiensis, Bacillus wiedmannii, Clostridium innoccuum, Kribella flavida, Lactobacillus plantarum, Obesumbacterium proteus*, and *Serratia liquefaciens*, The optional microorganisms may be grown in a similar fashion and be added to the microbial inoculum, as desired.

It is noted that the microbial inoculum comprising each *Paenibacillus xylanexedens, Pseudomonas fluorescens, Bacillus safensis, Streptomyces griseus, Micrococcus luteus*, and *Bacillus megaterium*, and optional other microorganisms, as herein described, may be stored for longer or shorter periods of time. Thus, for example, the microbial inoculum may be refrigerated at a temperature of from about 0° C. to about 4° C. for a period of about 1 week to about 4 weeks. Longer term storage, for a period of months or years, for example, may be achieved, for example, by adding a cryoprotective agent, such as glycerol in a concentration of from about 10% (v/v) to about 35% (v/v), and storing the cells in liquid nitrogen (−196° C.). Longer term storage may also be achieved by freeze drying (lyophilizing) the microbial inoculum, for example, by placing the microbial inoculum in a vial containing a lyoprotectant (10% skim milk for example), freezing the vial with a mixture of dry ice and alcohol, and vacuum drying the microbial inoculum while still frozen. In the process, the microbial cells are dehydrated. Upon sealing the vials, the vials containing the microbial inoculum can be stored for long periods of time, for example, for months or years, at 4° C.

Thus, to briefly recap, in accordance with an aspect of the present disclosure a microbial inoculum comprising at least the following microorganisms *Paenibacillus xylanexedens, Pseudomonas fluorescens, Bacillus safensis, Streptomyces griseus, Micrococcus luteus*, and *Bacillus megaterium*, together with an optional diluent or cryoprotective agent, may be prepared.

Next, in an aspect hereof, the microbial inoculum, following optional storage, can be used for formulation to form a bioremediation formulation. By the expression "formulating to form a bioremediation formulation", it is meant that microbial inoculum is combined with at least one other ingredient, including, but not limited to, a carrier and an auxiliary ingredient, whereby the microbial inoculum and the at least one other ingredient are mixed together, or blended, or homogenized, or otherwise prepared until a bioremediation formulation is formed. Bioremediation formulations, as used herein, are formulations comprising a microbial inoculum formulated together with one or more additional formulary ingredients.

Formulary ingredients constituting a bioremediation formulation may vary and include, for example, carriers and auxiliary ingredients, or mixtures thereof that are suitable for formulating a bioremediation formulation. In some embodiments, carriers and auxiliary ingredients, or mixtures thereof incorporated in the bioremediation formulation may be natural ingredients. In some embodiments, carriers, or auxiliary ingredients, or mixtures thereof, incorporated in the bioremediation formulation may be synthetic ingredients.

Example carriers that may be incorporated in the bioremediation formulations of the present disclosure include organic and inorganic carriers, including, for example, mineral earths, such as silicates, silica gels, talc, kaolins, limestone, lime, gypsum, chalk, clays, dolomite, diatomaceous earth, vermiculite, attapulgite, bentonite, montmorillonites, rock phosphate perlite; inorganic salts, such aluminum sulfate, calcium sulfate, copper sulfate, iron sulfate, magnesium sulfate, silicon sulfate, magnesium oxide; polysaccharides, such as cellulose, hydroxyethyl cellulose, carboxymethyl cellulose, starch, alginate, carrageenan; a plant seed, wood or nutshell meal, such as cereal meal, tree bark meal, wood meal, nutshell meal; grain flours such as flours from corn, rice, wheat, barley, sorghum, millet, oat, triticale, rye, buck wheat, and quinoa; peat or peat derived product such as lignite powder; compost, or mixtures thereof. The carriers may be provided in any form including as a solid, a powder, a crystal, a gel, a solution, a suspension, or a liquid.

Example auxiliary ingredients that may be incorporated in the bioremediation formulations of the present disclosure are, for example, ingredients which enhance microbial viability, such as skim milk, starch, glycerol or sugars, e.g. sucrose, trehalose or glucose; nutrients and growth stimulants, such as protein hydrolysates or humic acid, stabilizers, fillers, such as chitin, and formulation coating agents, such as chitosan. Auxiliary agents are generally included in smaller amounts, including, for example, about 10% (w/w) or less, or about 5% (w/w) or less.

It is further noted that the formulary ingredients and amounts thereof, as well as the operational techniques and conditions, may vary, depending on the use of the final formulation, which may vary, as hereinafter further described. In general, formulary ingredients can be contacted with a microbial inoculum and mixed or prepared until a bioremediation formulation is obtained. As will be clear to those of skill in the art, formulation conditions will generally be such that viable microorganisms are retained. In particular, high temperatures, for example, temperatures in excess of 40° C. are preferably avoided in the formulation process, and generally temperatures no higher than ambient temperature are preferred. Furthermore, other harsh conditions, such as the use of harsh chemicals or high shear forces, are generally preferably avoided. Any mixing or homogenizing equipment may be used to form the bioremediation formulation, including, any stirring, mixing or homogenizing equipment, such as a hand held electrically powered homogenizer, operated so that the constituent ingredients are mixed and a substantially homogenous mixture is obtained. Formulary ingredients may comprise, for example, from about 5% (w/w) up to about 95% (w/w), e.g. 10% (w/w), 15% (w/w), 20% (w/w), 25% (w/w), 30% (w/w), 35% (w/w), 40% (w/w), 50% (w/w), 60% (w/w), 70% (w/w), 80% (w/w), or 90% (w/w) of the bioremediation formulation, the balance comprising the microbial inoculum.

In some embodiments, the bioremediation formulation can comprise a microbial inoculum, together with an optional diluent, and a carrier which together constitute a substantive portion of the formulation, e.g. at least 90% (w/w), at least 95% (w/w), at least 96% (w/w), at least 97% (w/w), at least 98% (w/w), or at least 99% (w/w) of the bioremediation formulation. In some embodiments, the bioremediation formulation consists of, or consists substantially of, a microbial inoculum, together with an optional diluent, and a carrier. As hereinbefore noted, the bioremediation formulation in addition may contain auxiliary ingredients, such as nutrients, growth stimulants, and the like.

Furthermore, the concentration of the microbial inoculum or any other ingredients may be optimized or adjusted, for example, by preparing a plurality of sample bioremediation formulations, each provided with a different concentration of an ingredient, evaluating the suitability with reference to each formulation's suitability bioremedial efficacy, and then selecting one or more formulations which provide the most desirable bioremedial efficacy.

It is further noted that the physical constituency of the bioremediation formulations in accordance herewith can vary substantially and can include solid or semisolid formulations, such as gels, powders, and well as liquid formulations, including for example pourable or sprayable liquid formulations.

In one embodiment, the bioremediation formulation may be a formulation encapsulating a microbial inoculum. To aid in survival of microorganisms upon application to the substrate, the microbial inoculum may be encapsulated in, for example, a suitable polymeric matrix. In one example, encapsulation may comprise alginate beads such as described by Young et al., 2006, Encapsulation of plant growth-promoting bacteria in alginate beads enriched with humid acid, *Biotechnology and Bioengineering* 95:76-83. Those skilled in the art will appreciate that any suitable encapsulation material or matrix may be used. Encapsulation may be achieved using methods and techniques known to those skilled in the art. An encapsulation formulation can include nutrients or other auxiliary ingredients.

Upon formulation, the bioremediation formulations of the present disclosure can be directly used for bioremediation purposes, including, for example, by application to a glyphosate containing solid or liquid substrate. The term "substrate", as used herein, is intended to include any composition, material, product, substance, or portion thereof, for example, a surface area, or any environmental site which can contain glyphosate. Example substrates that can be used in accordance herewith include for example, soil contaminated with glyphosate, or water contaminated with glyphosate, including surface water or ground water. In one embodiment, the water may be contained for a period of time in a bioreactor, as illustrated in Example 2 below. The source of glyphosate and cause of contact between the substrate and glyphosate may vary, and can include, without limitation, residual quantities of glyphosate from a glyphosate containing herbicidal formulation for the treatment of crop or horticultural plants, present in the environment, the human food chain, or elsewhere.

Glyphosate can be detected using glyphosate analytical techniques known to the art, see: e.g. Botero-Coy et al., 2013, J. of Chromatography, 1292, 31: 132-141; Kuang et al., 2011, Overview of analytical techniques for herbicides in foods. In: Soloneski S, Larramendy M L, editors. Herbicides, theory and applications. Available from: http://www.intechopen.com/books/herbicides-theory-and-applications, accessed 15 Oct. 2019; and Noori et al., Sensors, 2018 18(9) 2961.

The bioremediation formulation of the present disclosure may be applied to a substrate once, or it may be applied repeatedly depending on, for example, the concentration of glyphosate present in or on the substrate. Furthermore, the quantity of the bioremediation formulation applied to the substrate may be varied and adjusted. Furthermore, the application techniques maybe varied and adjusted, for example, the bioremediation formulation may be sprayed upon the substrate, wiped onto the substrate, or poured in or on the substrate, for example. Furthermore, application conditions may be varied, for example, temperatures and total application time. The effect of such variations in application of the bioremediation formulation may be evaluated by a person of skill in the art, for example by evaluating glyphosate degradation using various application techniques or conditions and comparing glyphosate degradation under these different conditions and application techniques. As will be appreciated, by those of skill in the art, the evaluation results may be used to adjust application conditions and techniques to obtain a desirable glyphosate degradation effect.

In accordance with the present disclosure upon contact between the microbial inoculum in the bioremediation formulation and glyphosate, glyphosate is degraded and converted into other chemical compounds via one or more chemical reactions mediated by the microbial inoculum within the bioremediation formulation. In this respect, in accordance herewith the microorganisms present in the microbial inoculum remain viable once contact has been made between the bioremediation formulation and the substrate containing glyphosate, and the microbial organisms can grow while in contact with the substrate. Thus, the substrate can be said to be inoculated by the microbial inoculum. In general, contact between the residual glyphosate containing substrate and the bioremediation formulation is maintained for a sufficient period of time for the microorganisms to microbially biodegrade the residual glyphosate. The time period in this respect may vary and can be, for example, at least 1 day, at least 1 week, at least 1 month, at least 3 months, or longer. Furthermore, contact between the residual glyphosate containing substrate and the bioremediation formulation can be maintained for a sufficient period of time for the microorganisms to microbially biodegrade the residual glyphosate to certain desirable levels, for example, to less than about 75%, less than about 50%, less than about 25%, less than about 10%, or less than about 5% of the concentration present in or on a substrate prior to treatment with the bioremediation formulation. It will be understood that desirable glyphosate concentrations can vary depending on the substrate. Thus, for example, glyphosate tolerance levels in surface or drinking water supplies may differ from those in soil. Furthermore, glyphosate tolerance levels for a particular substrate may be determined, set, and adjusted from time to time, by governmental environmental regulatory agencies. Thus, in some embodiments, contact between the residual glyphosate containing substrate and the bioremediation formulation can be maintained for a sufficient period of time for the microorganisms to microbially biodegrade residual glyphosate to a glyphosate concentration deemed to be acceptable or safe in accordance with a guideline of a governmental environmental regulatory agency.

Depending on the substrate, the bioremediation formulation and its constituents may be removed upon glyphosate degradation, for example, by cleaning or washing the substrate. For certain substrates, however, soil substrates, for example, removal of the bioremediation formulation and its constituents may not be practical and the formulation and microorganisms may remain present for a prolonged period of time, possibly together with microorganisms natively associated with the substrate.

Figure 3:
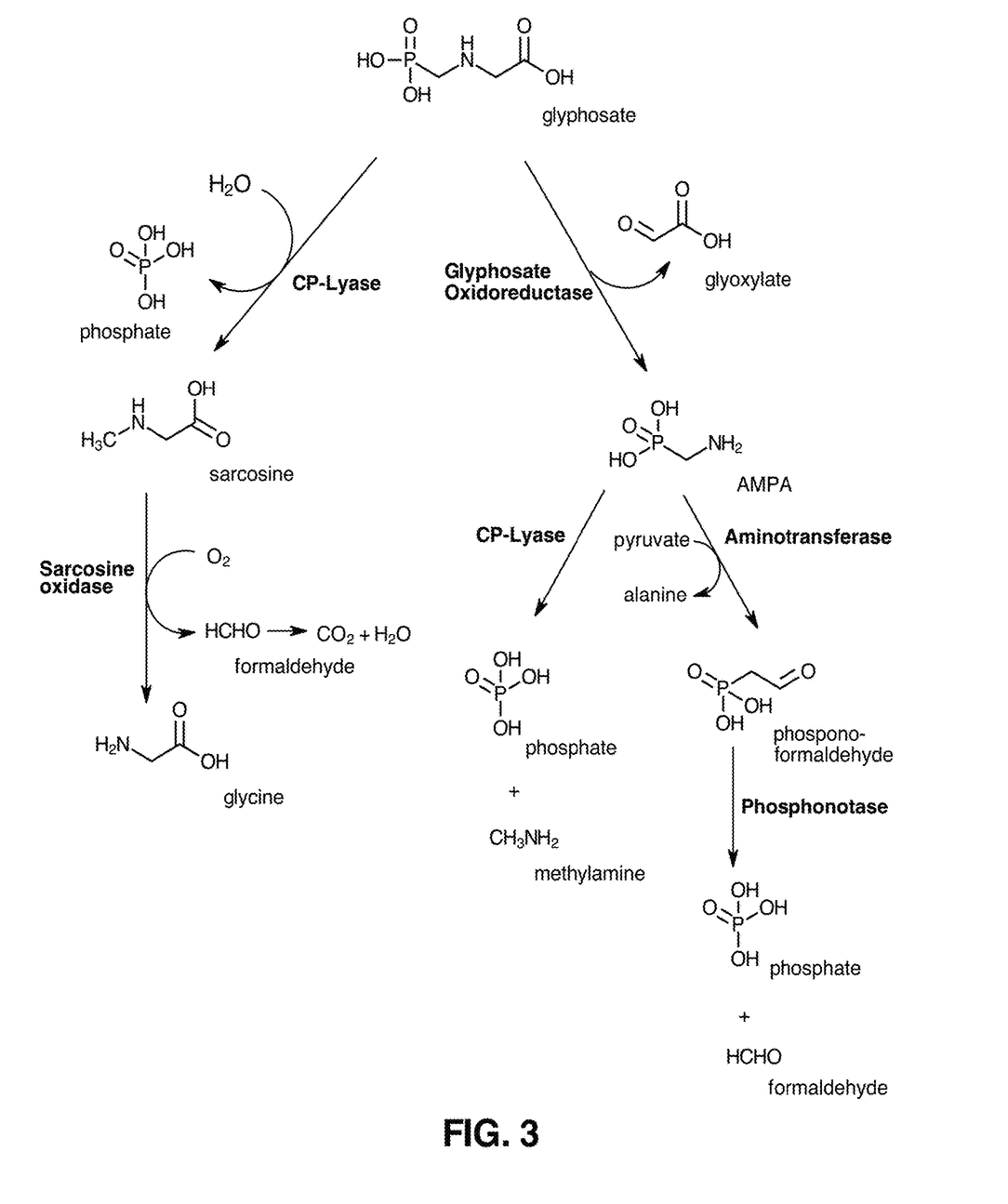
FIG. 3 depicts certain pathways for glyphosate degradation.

In one embodiment, the conversion can proceed according to the chemical reactions shown in FIG. 3. Thus, in one embodiment, glyphosate can be degraded into sarcosine, which in turn can be degraded into glycine and formaldehyde. The foregoing reactions may be catalyzed by microbial enzymes, CP-lyase and sarcosine oxidase, respectively. In one embodiment, glyphosate can be degraded into glyoxylate and aminomethyl phosphonic acid (AMPA) in a reaction catalyzed by the microbial enzyme glyphosate oxidoreductase. In one embodiment, AMPA, in turn may be degraded to methylamine in a reaction catalyzed by the microbial enzyme CP-lyase, or in another embodiment AMPA may be degraded to phoshono-formaldehyde in a reaction catalyzed by the microbial enzyme aminotransferase, which in turn may degraded to formaldehyde in a reaction catalyzed by the microbial enzyme phosphonotase.

Figure 4:
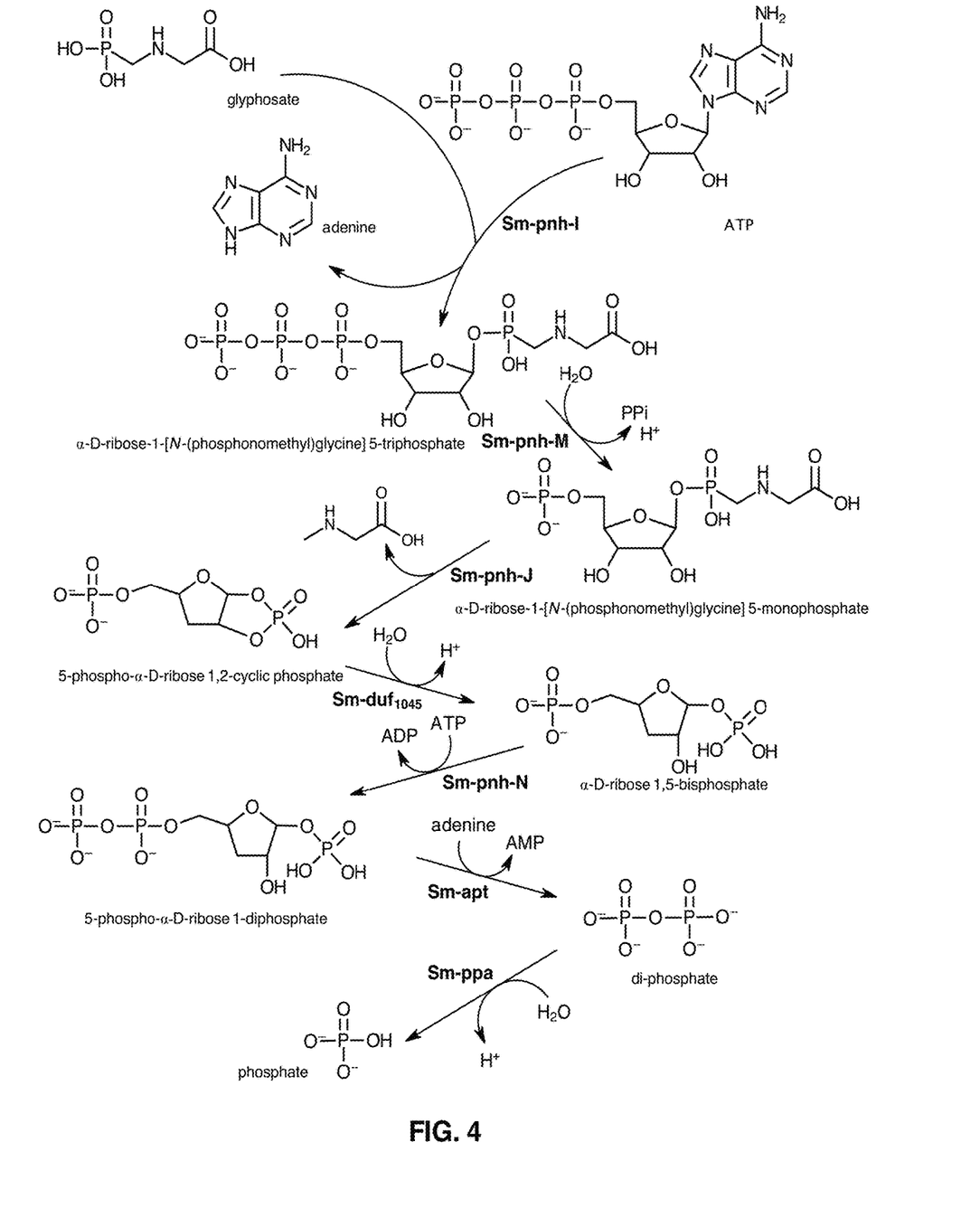
FIG. 4 depicts a certain other pathway for glyphosate degradation.

In another embodiment, the conversion can proceed according to the chemical reactions shown in FIG. 4. Thus, in one embodiment, glyphosate can be chemically bonded to adenosine triphosphate (ATP) and form α-D-ribose-1-[N-(phosphonomethyl)glycine] 5-triphosphate. Subsequently, α-D-ribose-1-[N-(phosphonomethyl)glycine] 5-triphosphate can be degraded in various steps to form α-D-ribose-1-[N-(phosphonomethyl)glycine] 5-monophosphate, 5-phospho-α-D-ribose 1,2 cyclic phosphate, α-D-ribose 1,5 biphosphate, and 5-phospho-α-D-ribose 1-diphosphate, as shown in FIG. 4. The foregoing reactions may be catalyzed by microbial enzymes, including the following: α-D-ribose-1-[N-(phosphonomethyl)glycine] 5-triphosphate synthase (Sm-pnhI), α-D-ribose-1-[N-(phosphonomethyl)glycine] 5-triphosphate diphosphatase (Sm-pnhM), α-D-ribose-1-[N-(phosphonomethyl)glycine] 5-phosphate C-P lyase (Sm-phnJ), phosphoribosyl 1,2-cyclic phosphate diesterase (Sm-duf$_{1045}$), ribose 1,5-biphosphate phosphokinase (Sm-phnN), adenine phosphoribosyltransferase (Sm-apt), and inorganic diphosphphatase (Sm-ppa), in accordance with the degradation pathway illustrated in FIG. 4.

Some or all of the reactions depicted in FIGS. 3 and 4 may occur upon application of the formulations of the present disclosure to a glyphosate containing substrate. Thus, it will be clear that in an example embodiment, the bioremediation formulation can, following application to a glyphosate containing substrate, biodegrade glyphosate, and generate one or more glyphosate breakdown products selected from aminomethyl phosphonic acid (AMPA), sarcosine, glyoxal, glycine, formaldehyde, phosphonoformaldehyde, α-D-ribose-1-[N-(phosphonomethyl)glycine] 5-triphosphate, α-D-ribose-1-[N-(phosphonomethyl)glycine] 5-monophosphate, 5-phospho-α-D-ribose 1,2 cyclic phosphate, α-D-ribose 1,5 biphosphate, and 5-phospho-α-D-ribose 1-diphosphate.

It is noted that, in addition to the chemical compounds shown in FIGS. 3 and 4, other glyphosate derivative compounds may be formed, as a result of glyphosate, or the other chemical compounds shown in FIGS. 3 and 4, contacting ingredients in the bioremediation formulation, including, for example, acetylglycine and N-tyrosyl-amine. Furthermore, prior to contact with the bioremediation formulation, glyphosate contained in the substrate may already have undergone some degradation, and some quantity of the chemical compounds shown in FIGS. 3 and 4 or other glyphosate derivatives, including, for example, acetylglycine and N-tyrosyl-amine, may already be present in the substrate.

In one specific example embodiment, the solid substrate can be soil or manure, for example for use as a soil fertilizer, and the microbial inoculum comprises cultured viable microorganisms of each of the species *Paenibacillus xylanexedens, Pseudomonas fluorescens, Bacillus safensis, Bacillus megaterium Streptomyces griseus* and *Micrococcus luteus*.

In one specific example embodiment, the liquid substrate can be water, and the microbial inoculum comprises a cultured viable microorganisms of each of the species *Paenibacillus xylanexedens, Pseudomonas fluorescens, Bacillus safensis, Bacillus megaterium, Streptomyces griseus, Micrococcus luteus, Rhanella aquatilis,* and *Bacillus marisflavus*.

In view of the foregoing, it will be clear that the present disclosure further relates to methods for bioremediation. Accordingly, in one aspect, the present disclosure provides, in at least one embodiment, a method for bioremediation of a residual glyphosate containing substrate, the method comprising:

(a) contacting a residual glyphosate containing substrate with a bioremediation formulation comprising a bioremedially effective amount of a microbial inoculum comprising cultured viable microorganisms of the species *Paenibacillus xylanexedens, Pseudomonas fluorescens, Bacillus safensis, Streptomyces griseus, Micrococcus luteus,* and *Bacillus megaterium*, the microorganisms remaining viable when the microbial inoculum is contacted with the glyphosate containing substrate; and (b) maintaining contact between the residual glyphosate containing substrate and the bioremediation formulation for a sufficient period of time to biodegrade the residual glyphosate.

In yet another aspect, the present disclosure provides a kit comprising a microbial inoculum for preparing a bioremediation formulation. Accordingly, in one aspect, the present disclosure provides, in at least one embodiment, a kit comprising a microbial inoculum comprising cultured viable microorganisms of the species *Paenibacillus xylanexedens, Pseudomonas fluorescens, Bacillus safensis, Streptomyces griseus, Micrococcus luteus*, and *Bacillus megaterium*, together with instructions for use of the kit. In some embodiments, the kit may comprise a concentrated microbial inoculum, for example, a concentration of at least $1\times10^5$ CFU, $1\times10^6$ CFU, $1\times10^7$ CFU, $1\times10^8$ CFU, $1\times10^9$ CFU, or $1\times10^{10}$ CFU per ml or per gram and a diluent, for example a saline solution, to prepare a diluted microbial inoculum. In some embodiments, the kit may comprise a carrier to formulate a bioremediation formulation comprising a bioremedially effective amount of a microbial inoculum. The instructions may be included with the kit (e.g. printed on paper and provided directly with the kit), and/or a reference may be provided for on-line access to the instructions, all of which are intended to be included herein. The instructions may additionally comprise further information regarding the products and its use, e.g. safety information.

In yet another aspect, the present disclosure provides a kit comprising a bioremediation formulation. Accordingly, in one aspect, the present disclosure provides, in at least one embodiment, a kit comprising a bioremediation formulation, the bioremediation formulation comprising a microbial inoculum comprising cultured viable microorganisms of the species *Paenibacillus xylanexedens, Pseudomonas fluorescens, Bacillus safensis, Streptomyces griseus, Micrococcus luteus*, and *Bacillus megaterium*, together with a carrier, and together with instructions for use of the kit. In some embodiments, the kit may comprise a concentrated bioremediation formulation and a diluent, for example a saline solution, to prepare a bioremedially effective bioremediation formulation. The instructions may be included with the kit (e.g. printed on paper and provided directly with the kit), and/or a reference may be provided for on-line access to the instructions, all of which are intended to be included herein. The instructions may additionally comprise further information regarding the products and its use, e.g. safety information.

In yet another aspect the present disclosure provides a use of a composition comprising cultured viable microorganisms. Accordingly, in one aspect the present disclosure provides, in at least one embodiment, a use of a microbial inoculum comprising cultured viable microorganisms of the species *Paenibacillus xylanexedens, Pseudomonas fluorescens, Bacillus safensis, Streptomyces griseus, Micrococcus luteus*, and *Bacillus megaterium* to prepare a bioremediation formulation for application to a residual glyphosate containing substrate to thereby biodegrade glyphosate, wherein the bioremediation formulation comprises an effective amount of the microbial inoculum of cultured viable microorganisms.

In yet another aspect, the present disclosure provides a use of a bioremediation formulation. Accordingly, in one aspect the present disclosure provides, in at least one embodiment, a use of a bioremediation formulation comprising a microbial inoculum of a bioremedially effective amount of cultured viable microorganisms comprising the species *Paenibacillus xylanexedens, Pseudomonas fluorescens, Bacillus safensis, Streptomyces griseus, Micrococcus luteus*, and *Bacillus megaterium* for application to a residual substrate containing glyphosate and thereafter biodegradation of the glyphosate.

Hereinafter are provided examples of specific embodiments of the compositions of the present disclosure and methods of the present disclosure. The examples are provided for illustrative purposes only, and are not intended to limit the scope in any way.

EXAMPLES

Example 1

Method for Obtaining a Microbial Inoculum and Preparing a Bioremediation Formulation A microbial stock culture of each *Paenibacillus xylanexedens, Pseudomonas fluorescens, Bacillus safensis, Streptomyces griseus, Micrococcus luteus*, and *Bacillus megaterium* was obtained for the preparation of a formulation containing the 6 different species of bacteria. Individual strains of bacteria that comprise the formulation were initially fermented in MRS culture medium, to produce 6 microbial inoculums, each comprising about $1\times10^9$ CFU/mL of the respective microbial species. The bacteria were harvested and centrifuged to obtain a cell pellet, which then was freeze-dried and the resulting dry cell mass weighed and the number of CFU/g calculated. A final microbial inoculum was then prepared by mixing a quantity of each of the dry cell mass materials to result in a microbial inoculum containing each of the species *Paenibacillus xylanexedens, Pseudomonas fluorescens, Bacillus safensis, Streptomyces griseus, Micrococcus luteus*, and *Bacillus megaterium*. The final microbial inoculum was prepared by diluting the individual inoculum of each species with saline (0.9% NaCl) and obtaining an inoculum of 0.1 gram of $1\times10^5$ CFU/g of each species. These diluted inoculums were mixed to obtain a mixture comprising a microbial inoculum of 0.6 gram comprising $1\times10^5$ CFU/g of each species together with the saline diluent. The resulting microbial inoculum was used to prepare bioremediation formulation, by mixing the microbial inoculum with a dihydroxymethyl cellulose at a 1:1 (w/w) ratio and thereby obtain a bioremediation formulation. The bioremediation formulation may be applied, for example, to glyphosate contaminated soils.

Example 2

Figure 5:
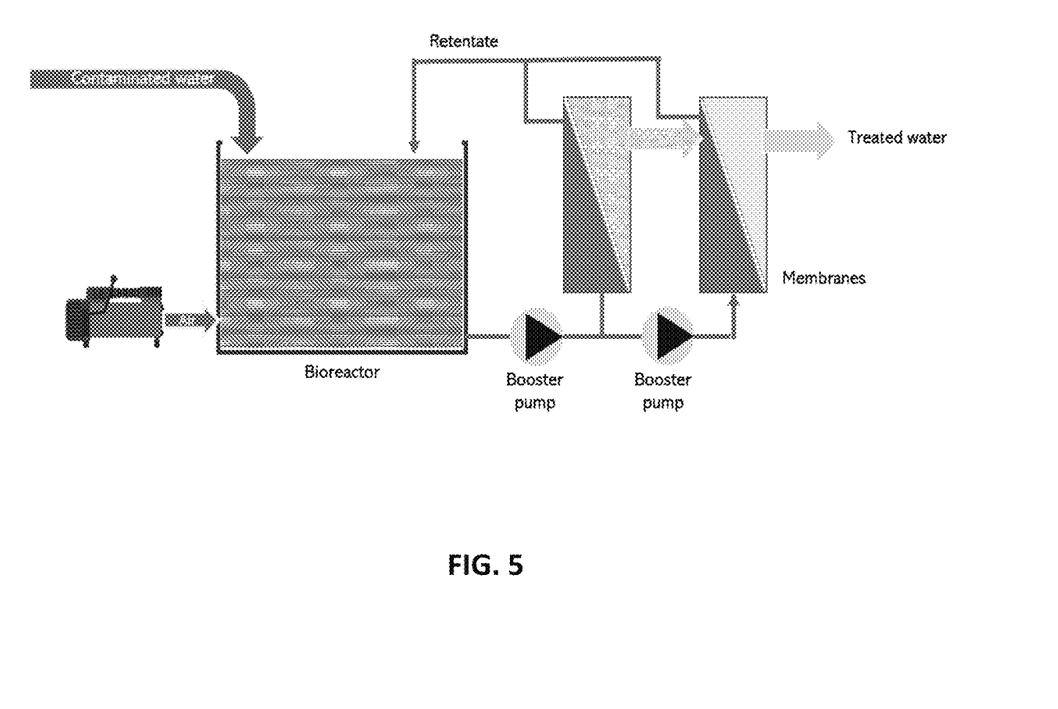
FIG. 5 depicts an example process for treating water contaminated with glyphosate with a bioremediation formulation.

Treatment of a Liquid Substrate Contaminated with Glyphosate with a Bioremediation Formulation A microbial inoculum consisting of *Paenibacillus xylanexedens, Pseudomonas fluorescens, Bacillus safensis, Streptomyces griseus, Micrococcus luteus*, and *Bacillus megaterium* can be prepared as described in Example 1 and diluted with a diluent, and, optionally, further formulated with a carrier or auxiliary ingredients to obtain a bioremediation formulation. A membrane bioreactor as illustrated in FIG. 5 is used for bioremediation by bioaugmentation of water contaminated with glyphosate. The bioremediation formulation can be added to glyphosate-contaminated water in an aerated bioreactor and can be allowed to grow in the presence of the contaminant glyphosate. The bioreactor suspension can be pumped through a first filter that permit the flow of treated water but retain the microbial organisms. The retentate, containing partially treated water and the microbial organisms can returned to the bioreactor. A portion of the treated water can then be pumped to a second filter. The treated water is passed through the second filter and the retentate can be returned to the bioreactor for further treatment. Glyphosate concentrations in the bioreactor and the treated water can be monitored and flow through the system can be adjusted in order to ensure the glyphosate concentrations in the treated water are acceptable. The process is illustrated in FIG. 5.

Example 3

Figure 6:
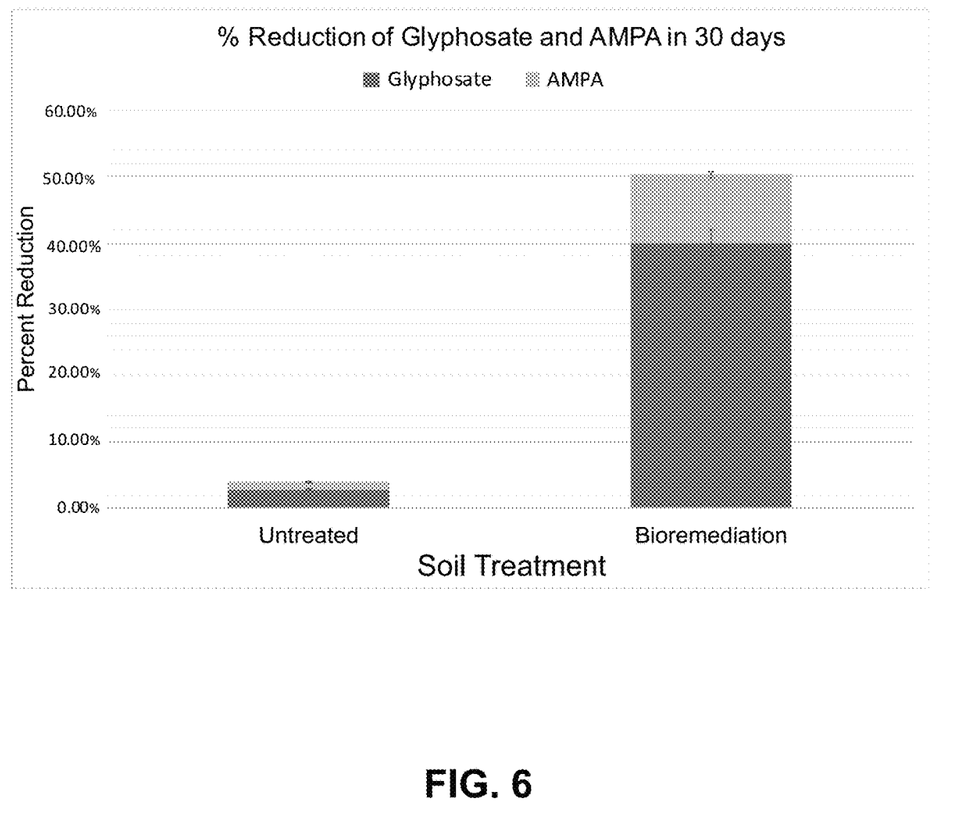
FIG. 6 is a bar graph showing certain results obtained in an experiment wherein an example bioremediation formulation comprising an inoculum of *Paenibacillus xylanexedens, Pseudomonas fluorescens, Bacillus safensis, Streptomyces griseus, Micrococcus luteus*, and *Bacillus megaterium* was used to treat for a period of 30 days a soil substrate contaminated with glyphosate. Shown is the percentage reduction of glyphosate and aminomethyl phosphonic acid (AMPA) in an untreated control soil sample (Control) and in a sample treated with the bioremediation formulation (Bioremediation).
Figure 7A:
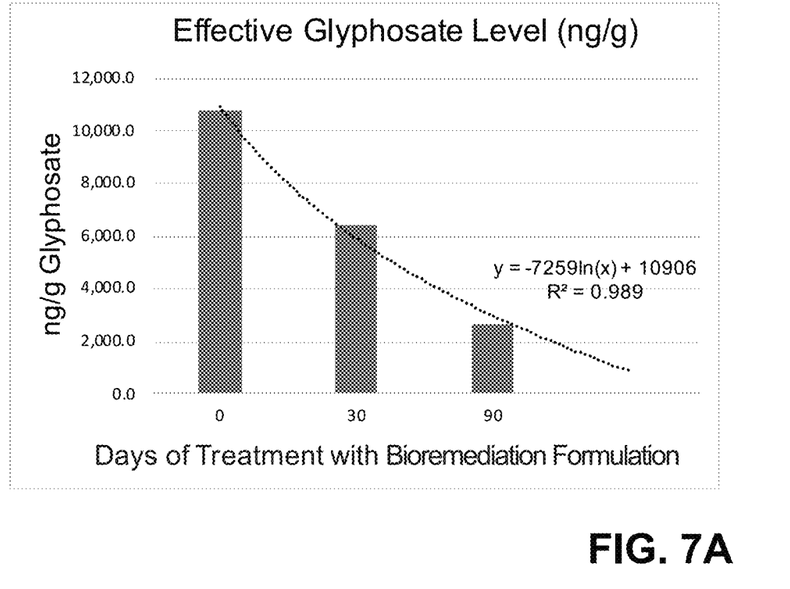
FIGS. 7A-7B are bar graphs showing certain results obtained in an experiment wherein an example bioremediation formulation comprising an inoculum of *Paenibacillus xylanexedens, Pseudomonas fluorescens, Bacillus safensis, Streptomyces griseus, Micrococcus luteus*, and *Bacillus megaterium* was used to treat a soil substrate contaminated with glyphosate. Shown is the amount of glyphosate (ng/gram soil) following 30 days and 90 days of treatment (FIG. 7A) and the percentage of glyphosate reduction following 30 and 90 days of treatment (FIG. 7B).
Figure 7B:
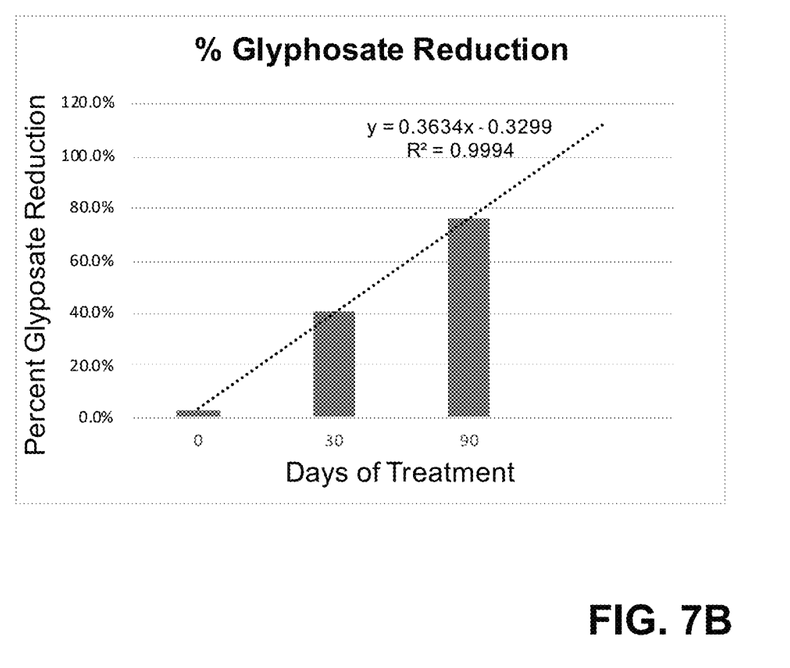

Treatment of a Solid Substrate Contaminated with Glyphosate with a Bioremediation Formulation A microbial inoculum comprising about $1\times10^5$ CFU/g *Paenibacillus xylanexedens, Pseudomonas fluorescens, Bacillus safensis, Streptomyces griseus, Micrococcus luteus,* and *Bacillus megaterium*, prepared as described in Example 1, was used to prepare a bioremediation formulation to remediate 1 cubic foot of soil contaminated with glyphosate at an amount of 10,000 ng/g. The microbial inoculum was mixed with carrier dihydroxy ethyl cellulose at 1:1 ratio carrier to obtain a bioremediation formulation comprising *Paenibacillus xylanexedens, Pseudomonas fluorescens, Bacillus safensis, Streptomyces griseus, Micrococcus luteus,* and *Bacillus megaterium*. The bioremediation formulation was incorporated into the soil by mixing the formulation in the soil and watering the soil with enough water to attain and maintain a 50% saturation for 90 days. The treated soil was maintained at ambient temperature for the entire duration (90 days) of the bioremediation procedure. A control of untreated glyphosate-containing soil was watered and incubated similarly without the addition of the bioremediation formulation for 90 days. Glyphosate and AMPA were by HPLC analysis by Health Research Institute Laboratories, in accordance with Wang S, Liu B, Yuan D, Ma J. A simple method for the determination of glyphosate and aminomethylphosphonic acid in seawater matrix with high performance liquid chromatography and fluorescence detection. Talanta, 2016 Dec. 1; 161:700-706. doi: 10.1016/j.talanta.2016.09.023. Epub 2016 Sep. 13. PMID: 27769468. The results are shown in FIGS. 6, 7A and 7B. As can be seen in FIG. 7A, following 30 days of incubation the amount of glyphosate in the treated soil was reduced from 10,000 ng/g to about 6,200 ng/g. Following 90 days treatment the amount of glyphosate was reduced further to about 2,500 ng/g. As further can be seen in FIG. 6 treatment with the bioremediation formulation resulted in a significant (40%) reduction in glyphosate as well as a significant (10%) reduction in AMPA (see: FIG. 6). Limited reduction (less than 5%) of glyphosate and AMPA was seen in untreated soil. FIG. 7B shows the percentile reduction in glyphosate amounts following 30 and 90 days of treatment corresponding with the amounts shown in FIG. 7A.

Example 4

Predicted Production of Glyphosate-Derived Phosphate Using a Flux-Balance Analysis Model.

DNA sequences obtained by whole genome sequencing from each of the individual bacterial species described in Example 1 were assembled using the assembly software SPAdes (Bankevich A, Nurk S, Antipov D, Gurevich A A, Dvorkin M, Kulikov A S, Lesin V M, Nikolenko S I, Pham S, Prjibelski A D, Pyshkin A V, Sirotkin A V, Vyahhi N, Tesler G, Alekseyev M A, Pevzner P A. SPAdes: a new genome assembly algorithm and its applications to single-cell sequencing. J Comput Biol. 2012 May; 19(5):455-77. doi: 10.1089/cmb.2012.0021. Epub 2012 Apr. 16. PMID: 22506599; PMCID: PMC3342519), and annotated using the annotation tool Prokka (Seemann T. Prokka: rapid prokaryotic genome annotation. Bioinformatics. 2014 Jul. 15; 30(14):2068-9. doi: 10.1093/bioinformatics/btu153. Epub 2014 Mar. 18. PMID: 24642063.).

Figure 8:
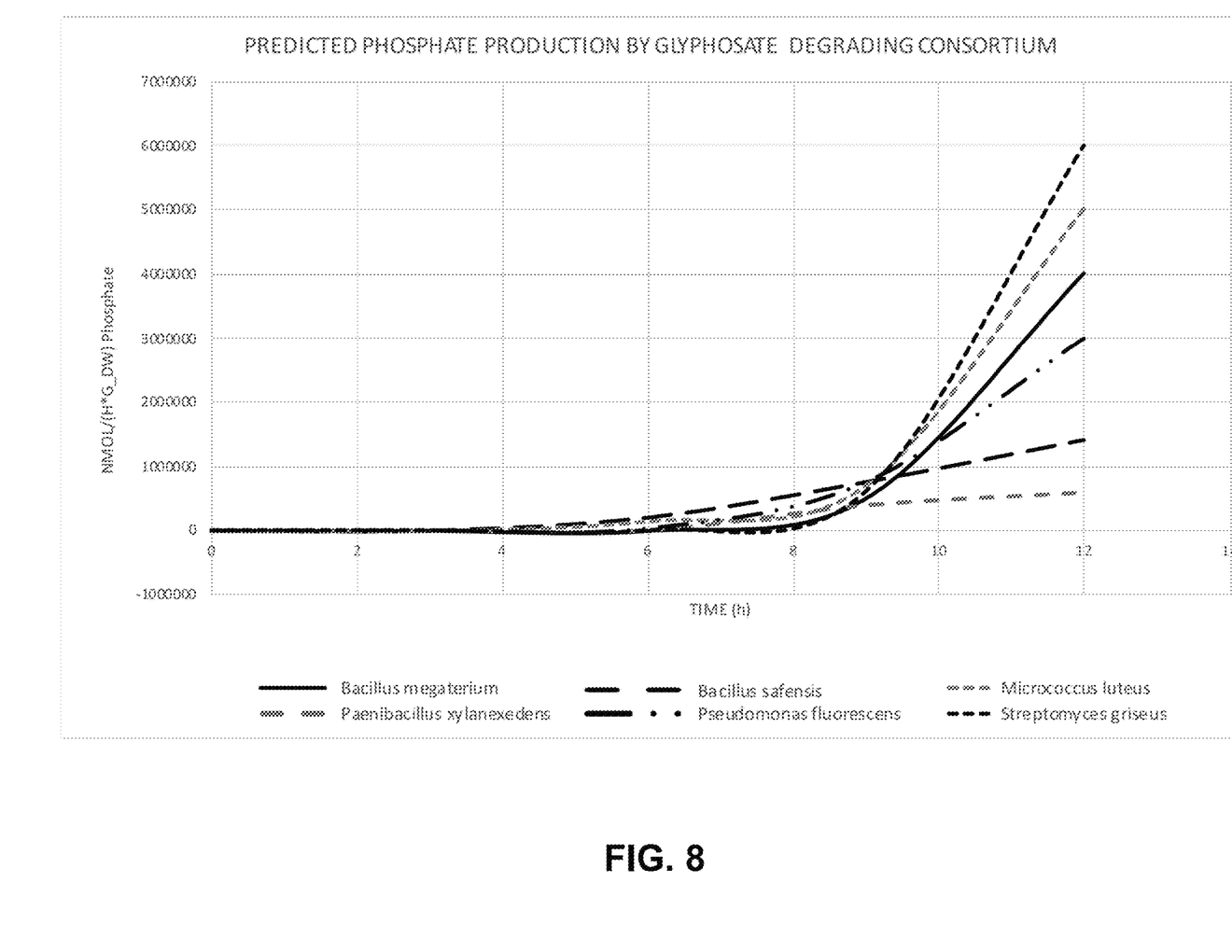
FIG. 8 is a graph showing the predicted production of phosphate in an in-vivo validated microbial community flux balance analysis (FBA) by an example bioremediation formulation of the present disclosure. Indicated is the predicted phosphate production by each of the species *Paenibacillus xylanexedens, Pseudomonas fluorescens, Bacillus safensis, Streptomyces griseus, Micrococcus luteus*, and *Bacillus megaterium*.

Following annotation, metabolic models were constructed using modelSEED (Devoid, S., Overbeek, R., DeJongh, M., Vonstein, V., Best, A. A., and Henry, C. (2013). "Automated genome annotation and metabolic model reconstruction in the SEED and model SEED," in Systems Metabolic Engineering, ed. H. S. Alper (Totowa, NJ: Humana Press), 17-45. doi: 10.1007/978-1-62703-299-5_2). All six metabolic models from individual strains were analyzed in a Steady-State Community, multi-organism COBRA model (Khandelwal R A, Olivier B G, Röling W F M, Teusink B, Bruggeman F J (2013) Community Flux Balance Analysis for Microbial Consortia at Balanced Growth. PLoS ONE 8(5): e64567) in a "complete culture medium" supplemented with glyphosate (1,000 nmol/L). The results of phosphate flux of the community model reconstruction was then plotted to visualize the individual contributions of each member of the consortium to the conversion of glyphosate to phosphate—the end product of complete degradation of glyphosate and AMPA. These results are summarized in FIG. 8. As can be seen in FIG. 8 all species, according to the metabolic model are contributing to glyphosate degradation and concomitant production of phosphate.

The invention claimed is:

1. A microbial inoculum comprising cultured viable microorganisms of the species *Paenibacillus xylanexedens, Pseudomonas fluorescens, Bacillus safensis, Streptomyces griseus, Micrococcus luteus*, and *Bacillus megaterium*.

2. The microbial inoculum according to claim 1, wherein the microbial inoculum further comprises one or more cultured viable microorganisms selected from the species *Rhanella aquatilis* and *Bacillus marisflavus*.

3. The microbial inoculum according to claim 1, wherein the microbial inoculum further comprises cultured viable microorganisms of at least one of the species *Acetobacter* spp., *Bacillus cereus, Bacillus oceanisediminis, Bacillus thuringiensis, Bacillus wiedmannii, Clostridium innoccuum, Kribella flavida, Lactobacillus plantarum, Obesumbacterium proteus*, and *Serratia liquefaciens*.

4. The microbial inoculum according to claim 1, wherein the microbial inoculum comprises from about $1\times10^2$ CFU per ml or per gram to about $1\times10^8$ CFU per ml or per gram of each of the microorganisms.

5. The microbial inoculum according to claim 1, wherein the microbial inoculum further comprises a diluent, which is optionally a saline solution.

6. The microbial inoculum according to claim 1, wherein the microbial inoculum further comprises a cryoprotectant, which is optionally glycerol in an amount of from about 10% (v/v) to about 35% (v/v).

7. The microbial inoculum according to claim 6, wherein the microbial inoculum of cultured viable microorganisms is dehydrated.

8. A bioremediation formulation for application to a residual glyphosate containing substrate, the bioremediation formulation comprising a microbial inoculum according to claim 1, together with a carrier, which is optionally a mineral earth; a polysaccharide; a plant seed, wood or nutshell meal; a grain flour; peat, a peat derived product; compost; diatomaceous earth; gypsum; vermiculite; attapulgite; cellulose; hydroxyethyl cellulose; carboxymethyl cellulose; alginate; or lignite powder.

9. The bioremediation formulation according to claim 8, wherein the microbial inoculum together with an optional diluent and the carrier constitutes at least about 95% (w/w) of the bioremediation formulation.

10. The bioremediation formulation according to claim 8, wherein the bioremediation formulation, following application to the glyphosate containing substrate, biodegrades glyphosate to generate one or more breakdown products selected from aminomethyl phosphonic acid (AMPA), sarcosine, glyoxal, glycine, N-acetylglycine, formaldehyde, and phosphonoformaldehyde.

11. The bioremediation formulation according to claim 8, wherein the bioremediation formulation, following application to the glyphosate containing substrate, biodegrades glyphosate to generate one or more breakdown products selected from «-D-ribose-1-[N-(phosphonomethyl)glycine] 5-triphosphate, α-D-ribose-1-[N-(phosphonomethyl) glycine] 5-monophosphate, 5-phospho-α-D-ribose 1,2 cyclic phosphate, α-D-ribose 1,5 biphosphate, and 5-phospho-α-D-ribose 1-diphosphate.

12. The bioremediation formulation according to claim 8, wherein the microorganisms in the microbial inoculum include a microbial amino acid metabolism which is not inhibited by glyphosate.

13. The bioremediation formulation according to claim 8, wherein the substrate is a solid substrate, which is optionally soil, or a liquid substrate.

14. The bioremediation formulation according to claim 13, wherein the liquid substrate is water, and the microbial inoculum further comprises cultured viable microorganisms of each of the species *Rhanella aquatilis* and *Bacillus marisflavis*.

15. A method for bioremediation of a residual glyphosate containing substrate, the method comprising:
    (a) contacting a residual glyphosate containing substrate with a bioremedially effective amount of a bioremediation formulation according to claim 8, the microorganisms remaining viable when the microbial inoculum is contacted with the glyphosate containing substrate; and
    (b) maintaining contact between the residual glyphosate containing substrate and the bioremediation formulation for a sufficient period of time for the microorganisms to microbially biodegrade the residual glyphosate.

16. The method according to claim 15, wherein the bioremediation formulation following application to the glyphosate containing substrate, biodegrades glyphosate to generate one or more breakdown products selected from aminomethyl phosphonic acid (AMPA), sarcosine, glyoxal, glycine, N-acetylglycine, formaldehyde and phosphonoformaldehyde.

17. The method according to claim 15, wherein the bioremediation formulation, following application to the glyphosate containing substrate, biodegrades glyphosate to generate one or more breakdown products selected from «-D-ribose-1-[N-(phosphonomethyl) glycine] 5-triphosphate, α-D-ribose-1-[N-(phosphonomethyl) glycine] 5-monophosphate, 5-phospho-α-D-ribose 1,2 cyclic phosphate, α-D-ribose 1,5 biphosphate, and 5-phospho-α-D-ribose 1-diphosphate.

18. The method according to claim 15, wherein the microorganisms in the microbial inoculum include a microbial amino acid metabolism which is not inhibited by glyphosate.

19. The method according to claim 15, wherein the substrate is a solid substrate, which is optionally soil, or a liquid substrate which is optionally surface water or ground water.

20. A kit comprising a microbial inoculum according to claim 1 together with instructions for use of the kit for application to a residual glyphosate containing substrate.

* * * * *